United States Patent
Burman et al.

(10) Patent No.: US 6,365,191 B1
(45) Date of Patent: Apr. 2, 2002

(54) FORMULATIONS OF PACLITAXEL, ITS DERIVATIVES OR ITS ANALOGS ENTRAPPED INTO NANOPARTICLES OF POLYMERIC MICELLES, PROCESS FOR PREPARING SAME AND THE USE THEREOF

(75) Inventors: Anand C. Burman; Rama Mukherjee; Dhiraj Khattar; Mukesh Kumar; Honey Bala; Rajiv Kumar Shrivastava, all of Uttar Pradesh (IN)

(73) Assignee: Dabur Research Foundation, Uttar Pradesh (IN)

( * ) Notice: Subject to any disclaimer, the term of this patent is extended or adjusted under 35 U.S.C. 154(b) by 0 days.

(21) Appl. No.: 09/667,417

(22) Filed: Sep. 21, 2000

Related U.S. Application Data

(63) Continuation-in-part of application No. 09/401,927, filed on Sep. 23, 1999.

(30) Foreign Application Priority Data

Feb. 17, 1999 (IN) .................................... 263/DEL/1999
Jul. 11, 2000 (IN) .................................... 641/DEL/2000

(51) Int. Cl.[7] .......................... A61K 9/14; A61K 31/74; A61K 9/127; A61K 9/50; A61K 31/335

(52) U.S. Cl. ................. 424/489; 424/78.08; 424/78.17; 424/450; 424/451; 424/501; 514/449

(58) Field of Search .............................. 424/489, 78.08, 424/78.17, 450, 451, 501; 514/449

(56) References Cited

U.S. PATENT DOCUMENTS

| | | | | |
|---|---|---|---|---|
| 5,449,513 A | * | 9/1995 | Yokoyama et al. ....... | 424/78.08 |
| 5,648,090 A | | 7/1997 | Rahman et al. ............ | 424/450 |
| 5,648,506 A | | 7/1997 | Desai et al. ................ | 549/510 |
| 5,681,846 A | * | 10/1997 | Trissel ........................ | 514/449 |
| 5,684,169 A | | 11/1997 | Hamada et al. ............. | 549/510 |

FOREIGN PATENT DOCUMENTS

| | | |
|---|---|---|
| EP | 0583955 | 2/1994 |
| WO | 9710849 | 3/1997 |
| WO | WO-9710849 | * 3/1997 |

OTHER PUBLICATIONS

Derwent Abstract JP11335267 Dated Dec. 7, 1999 XP002161131.

Kwon, G.S. et al. "Polymeric Micelles as New Drug Carriers" *Advanced Drug Delivery Rev.*, vol. 21 (1996) pp. 107–116.

Kwon, G.S. et al. "Block Copolymer Micelles as Long–Circulating Drug Vehicles" *Advanced Drug Delivery Rev.* vol. 16 (1995) pp. 295–309.

Kataoka K. et al. "Block Copolymer Micelles as Vehicles for Drug Delivery" *Journal of Controlled Release*, vol. 24 (1993) pp. 119–132.

Yokoyama, M. et al "Characterization and Anticancer Activity of the Micelle–Forming . . . " *Cancer Research* vol. 50 (1990) pp. 1693–1700.

Yokoyama, M. et al. "Toxicity and AntiTumor Activity Against Solid Tumors of Micelle–Forming . . . " *Cancer Research* vol. 51 (1991) pp. 3229–3236.

Yokoyama, M. et al. "Preparation of Micelle–Forming Polymer–Drug Conjugates" *Bioconjugate Chem.* vol. 3 (1992) pp. 295–301.

(List continued on next page.)

Primary Examiner—Thurman K. Page
Assistant Examiner—Blessing Fubara
(74) Attorney, Agent, or Firm—Ladas & Parry

(57) ABSTRACT

This invention relates to pharmaceutical formulations of paclitaxel, its derivatives or analogs entrapped into nanoparticles of co-polymeric micelles, a process for preparing the same and the use thereof.

17 Claims, 1 Drawing Sheet-

OTHER PUBLICATIONS

Kwon G. et al. "Enhanced Tumor Accumulation and Prolonged circulation Times of Micelle . . . " *Journal of Controlled Release.* vol. 29 (1994) pp. 17–23.

Yokoyama M. et al. "Influencing Factors on in Vitro Micelle Stability of Adriamycin–Block . . . " *Journal of Controlled Release* vol. 28 (1994) pp. 59–65.

Yokoyama M et al. "Improved Synthesis of Adriamycin–Conjugated Poly (Ethylene Oxide) . . . " *Journal of Controlled Release.* vol. 32 (1994) pp. 269–277.

Kwon G.S. et al. "Physical Entrapment of Adriamycin in AB Block Copolymer Micelles" *Pharmaceutical Research* vol. 12 No. 2 (1995) pp. 192–195.

Yokoyama, M. et al. "Introduction of Cisplatin into Polymeric Micelle" *Journal of Controlled Release* vol. 39 (1996) pp. 351–356.

La, S.B. et al. "Preparation and Characterization of the Micelle–Forming Polymeric . . . " *Journal of Pharmaceutical Sciences* vol. 85 (1996) pp. 85–90.

Zhang, X et al. Development of Amphiphilic Diblock Copolymers as *International Journal of Pharmaceutics* vol. 132 (1996) pp. 195–206.

Inoue, T. et al. "An AB Block Copolymer of Oligo (Methyl Methacrylate) and Poly . . . " *Journal of Controlled Release* vol. 51 (1998) pp. 221–229.

Kim, S.Y. et al. "Methoxy Poly (Ethylene Glycol) and E–Caprolactone Amphiphilic . . . " *Journal of Controlled Release* vol. 51(1998) pp. 13–22.

Yu, B.G. et al. "Polymeric Micelles for Drug Delivery: Solubilization and Haemolytic . . . " *Journal of Controlled Release* vol. 53 (1998) pp. 131–136.

Kwon, G. et al. "Block Copolymer Micelles for Drug Delivery: Loading and Release of . . . " *Journal of Controlled Release* vol. 48 (1997) pp. 195–201.

Jenkins, P. et al. "Taxol Branches Out" *Chemistry In Britain* (1996) pp. 43–46.

Arbuck, S.G. et al. "Clinical Development of Taxol" *Journal of The National Cancer Institute Monographs* vol. 15 (1993) pp. 11–24.

Long, H.J. "Paclitaxel (Taxol):A Novel Anticancer–Chemotherapeutic Drug" *Mayo Clin. Proc.* vol. 69 (1994) pp. 341–345.

Sharma, A. et al. "Novel Taxol Formulations: Preparation and Characterization . . . " *Pharmaceutical Research* vol. 11 No. 6 (1994) pp. 889–896.

* cited by examiner

FORMULATIONS OF PACLITAXEL, ITS DERIVATIVES OR ITS ANALOGS ENTRAPPED INTO NANOPARTICLES OF POLYMERIC MICELLES, PROCESS FOR PREPARING SAME AND THE USE THEREOF

This Application is a CIP of Ser. No. 09/401,927 filed Sep. 23, 1999.

This invention relates to pharmaceutical formulations of paclitaxel, its derivatives or analogs entrapped into nanoparticles of co-polymeric micelles, a process for preparing the same and the use thereof.

BACKGROUND OF THE INVENTION

Amongst the chemotherapeutic agents that have entered clinical testing in the last decade paclitaxel is one of the most promising candidates. It has shown impressive activities against ovarian cancer, breast cancer, non-small cell lung cancer, small cell lung cancer, squamous cell cancer of the head and neck and malignant melanomas. It is also undergoing clinical trials against several other malignancies.

It is preferred that paclitaxel be administered parenterally. Unfortunately, paclitaxel and many of its derivatives and analogs have exceedingly low solubilities in most physiologically acceptable aqueous solvents that would be compatible with intravascular administration.

There is one approved formulation of paclitaxel for parenteral administration in humans. This formulation contains the drug, 527 mg/ml of polyoxyethylated castor oil (Cremophor EL) and 49.7% v/v of absolute ethanol. Unfortunately, Cremophor has a potential to cause hypersensitivity reactions. The most common side effects of the available paclitaxel formulation are severe: hypotension, urticaria, angioedema and most notably anaphylactoid reactions with a risk of a fatal outcome. These serious side effects from the current drug formulation have made it necessary to pre-medicate the patients with diphendydramine, histamine $H_2$ antagonists or even corticosteroids.

Therefore, there is need for alternate formulations of paclitaxel, its derivatives or analogs. The present invention provides composition that makes it possible to reduce the ethanol concentration greatly, and to eliminate Cremophor completely from the formulations.

The formulations disclosed herein, contain nanoparticles of polymeric micelles that entrap/solubilize taxane analogs like paclitaxel without affecting their cytotoxic properties.

Nanometer size drug carriers with hydrophilic surfaces are found to evade recognition and uptake by the reticuloendothelial systems (RES) and thus can circulate in the blood for a long time. Another advantage of these hydrophilic nanoparticles is that, due to their extremely small size, the particles extravasate at the pathological sites such as solid tumors through passive targeting mechanism.

These nanoparticles of polymeric micelles besides keeping the drug in aqueous solution also help in increasing the circulation time in blood, in vivo.

SUMMARY OF THE INVENTION

The object if this invention is to overcome the drawbacks in the prior art by providing alternate formulations of paclitaxel, its derivatives or analogs by entrapping the drug in nanoparticles of polymeric micelles.

An important object of this invention is a process for the preparation of formulations of nanoparticles of polymeric micelles loaded with paclitaxel, its derivatives or analogs dispersed in aqueous solution, which can be diluted with aqueous intravenous fluids.

A further object of this invention is the use of formulations of this invention for the treatment of conditions arising out of excessive proliferation of cells.

Another object of this invention is the use of the formulations of this invention to target maximum amounts of drug to tumors and only negligible amounts to other tissues, which obviates the disadvantages associated with the prior art.

The formulations of this invention contain nanoparticles of polymeric micelles which contain paclitaxel, a derivative or analog thereof entrapped therein. The formulations contain paclitaxel, a derivative or analog thereof, a co-polymer, an anionic surfactant, a buffering agent and an intravenous aqueous diluting fluid.

DETAILED DESCRIPTION OF THE INVENTION

Figure 1:
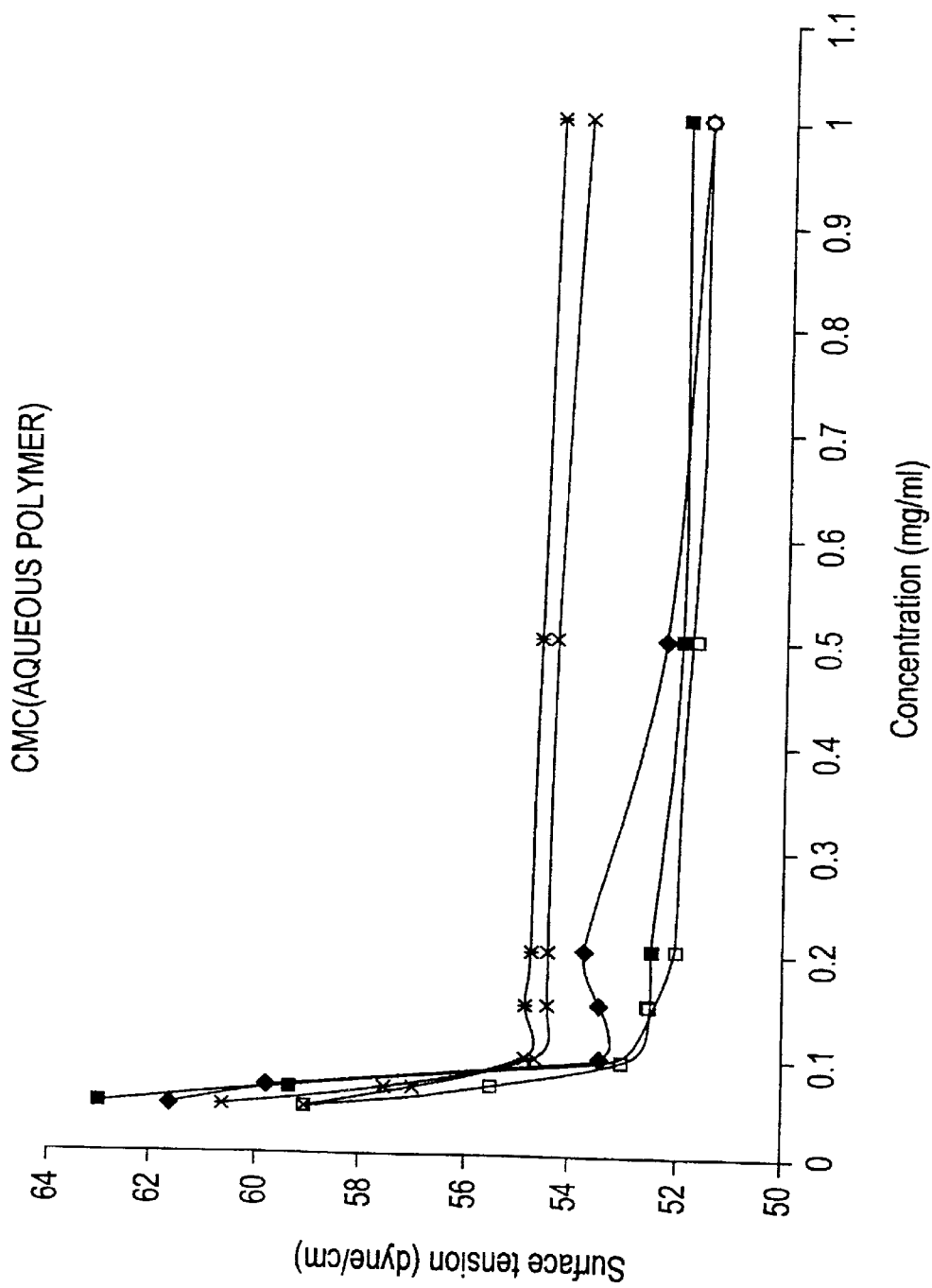
FIG. 1 shows the critical micelle concentration (CMC) of the polymer.

The present invention provides compositions and methods for the solubilization of taxane analogs (e.g. paclitaxel, its analogs or its derivatives) in nanoparticles of polymeric micelles in a pharmaceutically acceptable liquid vehicle that avoids the use of polyoxylethylated castor oils such as Cremophor EL, such that the drugs remain physically and chemically stable and can be administered intravascularly without undue toxicity from the undissolved drug and/or from the vehicle at drug doses contemplated to be effective to exhibit clinically significant effects on the excessive proliferation of cells (e.g. having significant anti-tumor activity). In a broader sense, the present invention describes a method to administer poorly water-soluble taxane analogs such as paclitaxel intravascularly. This circumvents the poor intestinal absorption of the drug as well as avoids the serious systemic adverse effects of Cremophor.

A detailed method of synthesis of the co-polymer for preparing the nanoparticles is described in U.S. patent application Ser. No. 09/401,927 filed in the U.S. PTO on Sep. 23, 1999 and is incorporated herein by reference. Nanoparticles are made of the co-polymer described in U.S. patent application Ser. No. 09/401,927. The polymer is first dissolved in a diluting fluid (e.g. dextrose solution) and anionic surfactant (e.g. sodium deoxycholate). The pH is adjusted to between 6.0 and 7.5 with a buffering agent. The drug (e.g. paclitaxel) is then loaded into these void nanoparticles. For this purpose the drug is dissolved in a suitable amount of an alcohol (e.g. preferably ethanol) and this solution of drug is then added to the solution of void nanoparticles. Immediately on addition, the drug moves from the hydrophilic aqueous environment to the hydrophobic core of the nanoparticles which are further stabilized by the anionic surfactant present on the surface of the nanoparticles.

The formulations of this invention can be administered parenterally or intravenously with a clinically acceptable, aqueous dilution fluid.

The compositions are prepared as described in U.S. patent application Ser. No. 09/401,927 and as described below:

a) dissolving at least one type of amphiphilic monomer, preferably two types of amphiphilic monomers in an aqueous medium to obtain micelles;

b) adding an aqueous cross-linking agent and optionally an activator and initiator;

c) subjecting the mixture to polymerization in the presence of an inert gas at 20° C. to 80° C., preferably between 30° C. to 40° C., until the polymerization of the micelles is complete;

d) purifying the nanoparticles of the co-polymeric micelles by dialysis to remove toxic monomers and other unreacted materials;

e) after purification as above, the solution of the void nanoparticles is sterilized by filtration and stored as such or optionally, lyophilized and stored for use later after dissolving in an intravenous dilution fluid;

f) adding an anionic surfactant;

g) adjusting the pH with a suitable buffering agent;

h) dissolving paclitaxel, its derivatives, or analogs in a suitable solvent, generally an alcohol preferably ethanol and adding this solution to the nanoparticle solution as a rapid fine stream;

i) optionally lypholizing the nanoparticles of co-polymerized micelles containing entrapped paclitaxel, its derivatives or analogs to obtain dry powder, and optionally;

j) reconstituting the nanoparticles in suitable medium for human or mammalian administration.

The completion of polymerization of the monomers in step c) is determined by monitoring the depletion of the monomers from the reaction mixture by HPLC.

Dialysis is carried out for 2–4 hours to eliminate unreacted monomers.

Nanoparticles of co-polymeric micelles are formed by the reaction/polymerization of the monomers in the reaction mixture. Random polymer chains are formed and are then cross-linked with each other with the help of a cross-linking agent. The amount of the cross-linking agent affects the amount of cross-linking in the polymer which in turn affects the compactness of the network formed. The compactness of this network has a direct bearing on the drug entrapment and consequently drug release from these nanoparticles. The more compact the network, the more difficult it is for the drug to be released.

The hydrophobic cores of these nanoparticles of co-polymeric micelles are composed of hydrophobic part of the co-polymers with the hydrophilic part extended outside towards the aqueous medium.

Amphiphilic monomers which form polymers through radical polymerization reaction are preferred. Preferred monomers are vinyl pyrrolidone, acrylic acid, alkyl acrylates having a chain length of $C_3$–$C_6$ and/or functionalized polyethylene glycol of a molecular weight 2000 to 6000, N-alkylacrylamide having a chain length of $C_3$ to $C_6$ and alkylcyanoacrylate having a chain length of $C_3$ to $C_6$. Two or more amphiphilic monomers are used.

A functionalized polyethylene glycol is a polyethylene glycol reacted to another organic compound containing a functional group. A preferred functionalized polyethylene glycol is polyethylene glycol ester of maleic anhydride. Polyethyleneglycol is reacted with maleic anhydride to form polyethylene glycol ester of maleic anhydride. Functionalized polyethyleneglycol may be covalently attached to the polymer chain of the nanoparticles of polymeric micelles with the polyethylene moiety protruding outside on the surface of the nanoparticles.

A preferred combination of amphiphilic monomers is vinylpyrrolidone and N-isopropyl acrylamide in the molar ratio of 10–50:50–90. Another preferred combination of amphilic monomers in vinylpyrrolidone, N-isopropyl acrylamide and monoester of polyethylene glycol maleic anhydride.

The buffering agents must be suitable for intravenous products. The buffering agent may be selected from acetate, borate, citrate, phosphate, or phthlate buffers, or agents such as diethanolamine, glycine, or glutamic acid.

The cross-linking agent whenever used is at least a bi-functional vinyl derivative. It can be more than bi-functional (i.e. it can have more than two reactive sites). A bi-functional vinyl derivative that can be used is N,N'-methylene bis acrylamide.

The initiators may be peroxide compounds, such as diacyl peroxide compounds such as benzoyl peroxide, diacetyl peroxide or dialkyl peroxides such as tertiary butyl peroxide and tertiary amyl peroxide or perdisulphate of 2,2'-azo bis isobutyronitrile.

Activators may be selected from tetramethylethylene diamine (TMED) and ferrous ammonium sulphate.

Any combination of initiator and activator can be used. Two or more initiators can be used. Two or more activators can be used.

The inert gas may be a gas such as nitrogen or argon.

The preferred anionic surfactant is sodium deoxycholate.

The dilution fluid may be selected from but is not limited to water, saline, dextrose 5% solution, dextrose 10% solution, dextrose and sodium chloride solution, sodium lactate solution, lactated Ringer solution, mannitol solution, mannitol with dextrose or sodium chloride solution, Ringer's solution, sodium chloride solution, sterile water for injection and multiple electrolyte solutions comprising varying combinations of electrolytes, dextrose, fructose and invert sugar. Preferably the dilution fluid is a fluid comprising dextrose and water.

Derivatives and analogs include but are not limited to:
1. 2-debenzoyl-2-methazidobenzoylpaclitaxel
2. Taxotere
3. Ring A contracted paclitaxel Derivatives
4. 10-Deacetyl Paclitaxel
5. 7-Deoxy Paclitaxel
6. Oxetane Ring (ring D) modified Paclitaxel
7. 2-Deoxy Paclitaxel
8. 2-Aroyl-2-Debenzoyl paclitaxel analogues
9. N-Benzoyl Modified Paclitaxel analogues
10. 2,3 cyclohexyl Paclitaxel analogues
11. 4-Deacetyl Paclitaxel analogues
12. 7,8-cyclopropane Paclitaxel
13. 7-Fluoropaclitaxel The % loading of paclitaxel, its analogues or its derivatives with respect to the polymer means that if in the formulation the concentration of the polymer is, for example, 1 mg/ml and the concentration of paclitaxel is 0.2 mg/ml, the drug is 20% by weight of the polymer. Since the total amount of the drug goes inside or is loaded in the nanoparticles, the drug loading is 20% by weight with respect to the polymer. The drug can be added up to a maximum loading of 400% w/w in the nanoparticles of co-polymeric micelles.

The concentration of the paclitaxel, its analogues or derivatives in the alcohol is 10 to 80 mg/ml.

The concentration of the co-polymer is from about 0.01 to 20 mg/ml, preferably 0.1 to 1mg/ml of the formulation.

The preferred concentration of the anionic surfactant is 0.01 to 0.5 mg/ml of the formulation.

The formulations described herein may be utilized to dissolve paclitaxel, its analogues or its derivatives in concentrations ranging from 0.1 to more than 18 mg/ml of the formulation. This range is contemplated to cover the administration of dosages necessary to yield active cytotoxic concentrations, in vivo to treat the conditions such as malignancies sensitive to these drugs.

The stable and parenterally acceptable novel formulations of nanoparticles of paclitaxel, its derivatives or its analogs can be utilized for the treatment of pathological conditions arising out of excessive proliferation of cells such as rheumatoid arthritis or cancer. The formulations can be used to treat cancers such as ovarian cancer, breast cancer, non-small cell lung cancer, small cell lung cancer, squamous cell cancer of the head and neck and malignant melanomas.

The formulations of this invention retain full cytotoxic activity as assessed in xenographs of malignant cells in mice. Exemplary formulations as shown herein have been found to be effective in causing regression of tumors of oral squamous cell carcinoma and murine metastatic melanomas in mice xenographs.

The following non-limiting examples are included to demonstrate preferred embodiments of the invention.

EXAMPLES 1–9

The polymer (5 mg) was dissolved in 5 ml of the diluting fluid followed by the addition of the anionic surfactant sodium deoxycholate (5 mg) to obtain a clear solution. Paclitaxel solution in absolute alcohol (20 mg/ml) was then added to the solution of polymer and the surfactant to obtain drug concentrations of 0.1, 0.15 and 0.2 mg/ml. Different diluting fluids were tried and the stability of the resulting drug solutions are tabulated below:

| Dilution Fluid | Polymer Conc. (mg/ml) | Sodium DOC Conc (mg/ml) | Paclitaxel Conc. (mg/ml) | % loading of Paclitaxel w.r.t. Polymer | Stability |
|---|---|---|---|---|---|
| Water for Injection | 1 | 1 | 0.10 | 10% | <1 hrs |
| Water for Injection | 1 | 1 | 0.15 | 15% | <1 hrs |
| Water for Injection | 1 | 1 | 0.20 | 20% | <1 hrs |
| Normal Saline | 1 | 1 | 0.10 | 10% | <1 hrs |
| Normal Saline | 1 | 1 | 0.15 | 15% | <1 hrs |
| Normal Saline | 1 | 1 | 0.20 | 20% | <1 hrs |
| 5% Dextrose | 1 | 1 | 0.10 | 10% | >8 hrs |
| 5% Dextrose | 1 | 1 | 0.15 | 15% | >6 hrs |
| 5% Dextrose | 1 | 1 | 0.20 | 20% | >4 hrs |

Dextrose had a stabilizing effect on the drug solubility as reflected in the stability of the drug solution.

EXAMPLES 10–12

Effect of Higher Drug Loading

The polymer (5 mg) was dissolved in 5 ml of the diluting fluid followed by the addition of the anionic surfactant sodium deoxycholate (5 mg) to obtain a clear solution. Paclitaxel solution in absolute alcohol (20 mg/ml) was then added to the solution of polymer and the surfactant to get drug concentrations of 0.2, 0.25 and 0.3 mg/ml. The stability of the resulting drug solutions are tabulated below:

| Dilution Fluid | Polymer Conc. (mg/ml) | Sodium DOC Conc (mg/ml) | Paclitaxel Conc. (mg/ml) | % loading of Paclitaxel w.r.t. Polymer | Stability |
|---|---|---|---|---|---|
| 5% Dextrose | 1 | 1 | 0.20 | 20% | >4 hrs |
| 5% Dextrose | 1 | 1 | 0.25 | 25% | <4 hrs |
| 5% Dextrose | 1 | 1 | 0.30 | 30% | <4 hrs |

More than 20% drug loading with respect to the polymer resulted in reduced stability of the drug solution.

EXAMPLES 13–14

Effect of Higher Concentration of Dextrose

The polymer (5 mg) was dissolved in 5 ml of the diluting fluid followed by the addition of the anionic surfactant sodium deoxycholate (5 mg) to obtain a clear solution. Paclitaxel solution in absolute alcohol (20 mg/ml) was then added to the solution of polymer and the surfactant to obtain drug concentrations of 0.2 mg/ml. Different diluting fluids were tried and the stability of the resulting drug solutions are tabulated below:

| Dilution Fluid | Polymer Conc. (mg/ml) | Sodium DOC Conc (mg/ml) | Paclitaxel Conc. (mg/ml) | % loading of Paclitaxel w.r.t. Polymer | Stability |
|---|---|---|---|---|---|
| 5% Dextrose (pH 5.1) | 1 | 1 | 0.20 | 20% | >4 hrs |
| 10% Dextrose (pH 5.1) | 1 | 1 | 0.20 | 20% | >6 hrs |

10% dextrose had a more stabilizing effect on the solution as compared to 5% dextrose. The same was also reflected on the better solution clarity with 10% dextrose.

EXAMPLES 15–17

Effect of PH on Solution Stability at 20% Drug Loading

The polymer (5 mg) was dissolved in 5 ml of the diluting fluid followed by the addition of the anionic surfactant sodium deoxycholate (5 mg) to obtain a clear solution. pH of the resulting solution was adjusted with sodium citrate. Paclitaxel solution in absolute alcohol (20 mg/ml) was then added to the solution of polymer and the surfactant to obtain drug concentrations of 0.2 mg/ml. Results are tabulated below:

| Dilution Fluid | Polymer Conc. (mg/ml) | Sodium DOC Conc (mg/ml) | Sodium Citrate (mg/ml) | pH | Paclitaxel Conc. (mg/ml) | Stability |
|---|---|---|---|---|---|---|
| 10% Dextrose (pH 3.9) | 1 | 1 | 0.00 | 6.28 | 0.20 | <1 hrs |
| 10% Dextrose | 1 | 1 | 0.06 | 6.36 | 0.20 | >6 hrs |

-continued

| Dilution Fluid | Polymer Conc. (mg/ml) | Sodium DOC Conc (mg/ml) | Sodium Citrate (mg/ml) | pH | Paclitaxel Conc. (mg/ml) | Stability |
|---|---|---|---|---|---|---|
| (ph 3.9) 10% Dextrose (ph 3.9) | 1 | 1 | 0.12 | 6.53 | 0.20 | >4 hrs |

EXAMPLE 18

Determination of CMC of Polymer

Critical Micelle Concentration (CMC) of the polymer was determined using aqueous solutions of concentration ranging from 0.01 to 1.0 mg/ml. CMC was found to be in the range of 0.1–0.2 mg/ml as shown in FIG. 1.

EXAMPLES 19–23

Effect of Reduction of Polymer/Sodium DOC on Drug Loading

The requisite amount of polymer was dissolved in 5 ml of the diluting fluid followed by the addition of requisite amount of anionic surfactant sodium deoxycholate to obtain the concentrations shown in the table below. pH of the resulting solution was adjusted to 6.4–6.8 with sodium citrate. Paclitaxel solution in absolute alcohol (20 mg/ml) was then added to the solution of polymer and the surfactant to obtain drug concentrations of 0.2 mg/ml. Results are tabulated below:

| Dilution Fluid | Polymer Conc. (mg/ml) | Sodium DOC. (mg/ml) | pH | Paclitaxel Conc. (mg/ml) | Stability |
|---|---|---|---|---|---|
| 10% Dextrose | 1 | 1 | 6.45 | 0.20 | >6 hrs |
| 10% Dextrose | 0.5 | 0.5 | 6.44 | 0.20 | >6 hrs |
| 10% Dextrose | 0.25 | 0.25 | 6.46 | 0.20 | >6 hrs |
| 10% Dextrose | 0.125 | 0.125 | 6.47 | 0.20 | >6 hrs |
| 10% Dextrose | 0.0625 | 0.0625 | 6.44 | 0.20 | <6 hrs |

EXAMPLES 24–27

Effect of Reduction of Sodium DOC on Drug Loading

The polymer (0.625 mg) was dissolved in 5 ml of the diluting fluid followed by the addition of the anionic surfactant sodium deoxycholate to obtain a clear solution. pH of the resulting solution was adjusted to 6.4–6.8 with sodium citrate.

Paclitaxel solution in absolute alcohol (20 mg/ml) was then added to the solution of polymer and the surfactant to obtain drug concentrations of 0.2 mg/ml. Results are tabulated below:

| Dilution Fluid | Polymer Conc. (mg/ml) | Sodium DOC. (mg/ml) | Paclitaxel Conc. (mg/ml) | Stability |
|---|---|---|---|---|
| 10% Dextrose | 0.125 | 0.03125 | 0.20 | <1 hrs |
| 10% Dextrose | 0.125 | 0.0625 | 0.20 | <2 hrs |
| 10% Dextrose | 0.125 | 0.09375 | 0.20 | >6 hrs |
| 10% Dextrose | 0.125 | 0.125 | 0.20 | >6 hrs |

EXAMPLES 28–35

Optimization of Drug Loading

The requisite amount of the polymer was dissolved in 5 ml of the diluting fluid followed by the addition of requisite amount of the anionic surfactant sodium deoxycholate to obtain the concentrations shown in the table below. pH of the resulting solution was adjusted to 6.4–6.8 with sodium citrate. Paclitaxel solution in absolute alcohol (20 mg/ml) was then added to the solution of polymer and the surfactant to get drug concentrations of 0.2, 0.5, 0.6, 0.7, 0.8, 2.4, 3.2, 4.0, and 10 mg/ml. Results are tabulated below:

| Dilution Fluid | Polymer Conc. (mg/ml) | Sodium DOC. (mg/ml) | Paclitaxel Conc. (mg/ml) | Stability |
|---|---|---|---|---|
| 10% Dextrose | 0.125 | 0.125 | 0.20 | >6 hrs |
| 10% Dextrose | 0.125 | 0.125 | 0.50 | <4 hrs |
| 10% Dextrose | 0.125 | 0.125 | 0.80 | <2 hrs |
| 10% Dextrose | 0.125 | 0.125 | 2.4 | <1 hrs |
| 10% Dextrose | 0.125 | 0.125 | 3.2 | <30 min |
| 10% Dextrose | 0.125 | 0.125 | 4.0 | <15 min |
| 10% Dextrose | 0.125 | 0.125 | 10.0 | <5 min |
| 10% Dextrose | 0.2 | 0.2 | 0.80 | <3 hrs |
| 10% Dextrose | 0.3 | 0.3 | 0.80 | <2 hrs |
| 10% Dextrose | 0.3 | 0.3 | 0.70 | <4 hrs |
| 10% Dextrose | 0.3 | 0.3 | 0.60 | <6 hrs |
| 10% Dextrose | 0.3 | 0.3 | 0.50 | >6 hrs |

EXAMPLES 36–40

Effect of Reduction of Sodium DOC on Drug Loading

The polymer (1.5 mg) was dissolved in 5 ml of the diluting fluid followed by the addition of the anionic surfactant sodium to obtain concentrations of 0, 0.10, 0.15, 0.20 and 0.25 mg/ml. pH of the resulting solution was adjusted to 6.4–6.8 with sodium citrate. Paclitaxel solution in absolute alcohol (20 mg/ml) was then added to the solution of polymer and the surfactant to obtain drug concentrations of 0.6 mg/ml. Results are tabulated below:

| Dilution Fluid | Polymer Conc. (mg/ml) | Sodium DOC. (mg/ml) | Paclitaxel Conc. (mg/ml) | Stability |
|---|---|---|---|---|
| 10% Dextrose | 0.3 | 0 | 0.60 | <30 min |
| 10% Dextrose | 0.3 | 0.10 | 0.60 | <1 hrs |
| 10% Dextrose | 0.3 | 0.15 | 0.60 | <4 hrs |
| 10% Dextrose | 0.3 | 0.2 | 0.60 | >8 hrs |
| 10% Dextrose | 0.3 | 0.25 | 0.60 | >8 hrs |

The Preferred Composition

Drug Solution paclitaxel (100 mg) in ethanol (5 ml) to obtain a clear solution having a concentration of 20 mg/ml and filtered through 0.2μ filter.

Infusion Vehicle is obtained by separately dissolving 30 mg of the polymer, 30 mg of sodium citrate and 20 mg of the anionic surfactant sodium deoxycholate in 100 ml of Dextrose (10%) solution and filtering through 0.2μ filter.

Formulation for Infusion

The required amount of the drug solution (3 ml) is added to the vehicle to obtain a drug concentration of 0.6 mg/ml. The perfusion fluid is stable for more than 12 hrs without any apparent signs of precipitation of drug. Stability is also indicated by the fact that more than 90% of the drug is available in solution form at the end of 24 hrs, when analyzed by HPLC.

Loss of Drug During Passage Through 0.2μ In-Line Filter in a I.V. Set

A formulation of the preferred composition (100 ml) as given above was passed through an infusion set containing 0.21μ in-line filter, at a flow rate of about 3 ml per minute to simulate the actual bedside situation. The loss of drug during passage through the 0.2μ in-line filter was not more than 5%.

What is claimed is:

1. A formulation containing nanoparticles of polymeric micelles containing a drug selected from paclitaxel, a derivative or an analogs thereof physically entrapped therein, said formulation comprising paclitaxel, the derivative or the analogs, an alcohol, a co-polymer, an anionic surfactant, a buffering agent and an intravenous aqueous diluting fluid.

2. The formulation as claimed in claim 1, wherein the copolymer is formed from at least two amphiphilic monomers selected from the group consisting of vinylpyrrolidone, acrylic acid, alkyl acrylates having a chain length of $C_3$–$C_6$, functionalized polyethylene glycol of a molecular weight of 2000 to 6000, N-alkylacrylamide having a chain length of $C_3$ to $C_6$ and alkylcyanoacrylate having a chain length of $C_3$ to $C_6$.

3. The formulation as claimed in claim 1, wherein the co-polymer is formed from vinylpyrrolidone, N-isopropyl acrylamide, and functionalized polyethylene glycol.

4. The formulation as claimed in claim 1, wherein the concentration of the drug about 0.1 to 20 mg/ml of the formulation.

5. The formulation as claimed in claim 1, wherein the concentration of co-polymer is about 0.01 to 20 mg/ml of the formulation.

6. The formulation as claimed in claim 1, wherein the anionic surfactant is sodium deoxycholate.

7. The formulation as claimed in claim 6, wherein the concentration of sodium deoxycholate is about 0.01 to 20 mg/ml of the formulation.

8. The formulation as claimed in claim 1, wherein the buffering agent is suitable for intravenous administration.

9. The formulation a claimed in claim 1, wherein the pH is between 6.0 to 7.5.

10. The formulation as claimed in claim 1, wherein the intravenous aqueous diluting fluid is a dextrose solution.

11. The formulation as claimed in claim 1, wherein the concentration of paclitaxel in the alcohol is 10 to 80 mg/ml.

12. A method of preparing a formulation for intravascular administration comprising the steps of:
    a) dissolving a co-polymer in an intravenous dilution fluid;
    b) adding an anionic surfactant to the solution of step "a";
    c) adjusting the pH of the resulting solution; and
    d) adding an alcoholic solution of paclitaxel, its derivatives or analogs to the above solution.

13. A formulation prepared by the method of claim 12.

14. A method of treating a condition arising from excessive proliferation of cells comprising administering a formulation of claim 1 to a patient in need thereof.

15. The method according to claim 14, wherein the condition is cancer.

16. The method according to claim 14, wherein the condition is a tumor.

17. The method according to claim 14, wherein the condition is rheumatoid arthritis.

* * * * *